United States Patent [19]

Katoh et al.

[11] Patent Number: 5,571,889

[45] Date of Patent: Nov. 5, 1996

[54] POLYMER CONTAINING MONOMER UNITS OF CHEMICALLY MODIFIED POLYASPARTIC ACIDS OR THEIR SALTS AND PROCESS FOR PREPARING THE SAME

[75] Inventors: Toshio Katoh, Saitama-ken; Akinori Nagatomo, Kanagawa-ken; Hiroaki Tamatani, Kanagawa-ken; Masanobu Ajioka, Kanagawa-ken; Akihiro Yamaguchi, Kanagawa-ken, all of Japan

[73] Assignee: Mitsui Toatsu Chemicals, Inc., Tokyo, Japan

[21] Appl. No.: 450,117

[22] Filed: May 25, 1995

[30] Foreign Application Priority Data

May 30, 1994 [JP] Japan ................. 6-116981

[51] Int. Cl.⁶ ............................... C08G 69/10
[52] U.S. Cl. ............... 528/328; 528/499; 525/419; 525/420
[58] Field of Search .............. 528/328, 499; 525/419, 420

[56] References Cited

U.S. PATENT DOCUMENTS 5,373,086 12/1994 Koskans et al. .............. 528/328

FOREIGN PATENT DOCUMENTS 658586 6/1995 European Pat. Off. .
WO94/20563 9/1994 WIPO .

OTHER PUBLICATIONS

M. De L. Machado et al, *Water–Soluble Polyamides as Potential Drug Carriers*, V, Applied Macromolecular Chemistry And Physics, 195, 1992. pp. 35–56.

Primary Examiner—Shelley A. Dodson
Assistant Examiner—Michael A. Williamson
Attorney, Agent, or Firm—Burns, Doane, Swecker & Mathis

[57] ABSTRACT

A polymer containing the following monomer unit (I) and/or (II):

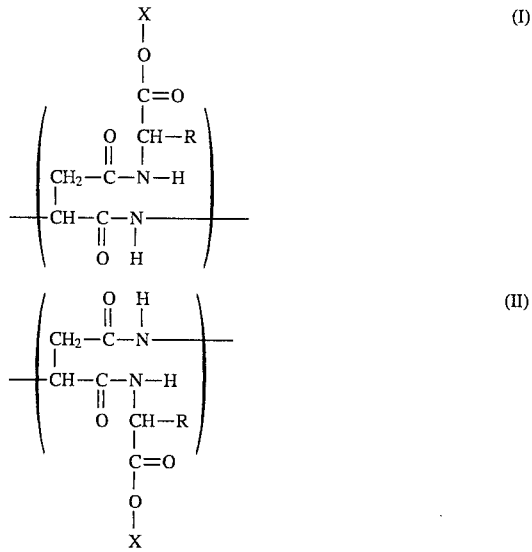

and a process for preparing the polymer which comprises, in ring opening reaction of the polysuccinimide, opening the ring of polysuccinimide by using an amino acid ester having an extremely high reactivity in place of an α-amino acid having an extremely low reactivity. The polymer is characterized by having no irritation to organisms (e.g., eyes and skin), and for example, the polymer is useful in the industrial fields of fields of medical supplies, health, beauty and sanitary aids, quasi-pharmaceuticals, and the like.

7 Claims, No Drawings

POLYMER CONTAINING MONOMER UNITS OF CHEMICALLY MODIFIED POLYASPARTIC ACIDS OR THEIR SALTS AND PROCESS FOR PREPARING THE SAME

BACKGROUND OF THE INVENTION i) Field of the Invention

The present invention relates to a polymer having an amino acid residue or an amino acid ester residue as a pendant group in at least a part of a monomer unit, and a process for preparing it. More specifically, the present invention relates to a process for preparing a polymer by reacting polysuccinimide with an amino acid ester.

That is to say, the present invention relates to a polymer which can be obtained by reacting polysuccinimide with an amino acid ester in the presence or absence of a basic catalyst and which is not irritant to organisms (e.g., eyes and skin) and which has an amino acid residue or an amino acid ester residue as a pendant group in at least a part of a monomer unit, and a process for preparing it.

The polymer of the present invention is characterized by having no irritation to organisms (e.g., eyes and skin), and for example, the polymer is useful in the industrial fields of medical supplies, health, beauty and sanitary aids, quasi-pharmaceuticals (in Japanese: "IYAKU-BUGAIHIN" defined in the Drugs, Cosmetics and Medical Instruments Act of Japan), and the like. Concretely, for example, the polymer is useful in the industrial fields of carriers for drugs, cosmetics, perfumes, surface active agents, food additives (thickeners, stabilizers, moisturizers, noodle modifiers, coagulants, pH adjustors, bacteriostats and the like).

ii) Description of the Prior Art

Aspartamides obtained by ring opening reaction of polysuccinimide with various amines have been known ever since a long time ago.

For example, in Journal of Medical Chemistry, Neri et al., Vol. 16, No. 8, p. 893–897, (1973), there has been disclosed a technique in which the rings of polysuccinimide are opened by reaction with ethanolamine to produce 2-hydroxyethylaspartamide. This product is considered to be useful as a plasma expander.

For example, U.S. Pat. No. 4,363,797 (Jacquet et al.) has disclosed a technique in which the rings of polysuccinimide are opened by reaction with cysteamine or taurine to produce polyaspartamide. This product is considered to be useful as a cosmetic composition.

However, the present inventors observed that the polyaspartamide obtained by ring opening reaction of the polysuccinimide with cysteamine is an irritant when they carried out a rabbit eye mucous membrane irritation test (described hereinafter).

Therefore, it has been apparent that the polyaspartamide, which is obtained by ring opening reaction of the polysuccinimide with cysteamine according to the prior art, does not always provide a polymer having no irritation to organisms.

With regard to this problem, it is not clearly definite what substance causes the irritation to the rabbit eye mucous membrane. However, the present inventors have presumed that the amine such as cysteamine used for the ring opening of the polysuccinimide is concerned with the irritation in any manner.

Thus, in view of the above-mentioned problem of the prior art, the present inventors have intensively conducted investigations based on a conception to use a compound, which is safe to organisms and environments, for the ring opening reaction of the polysuccinimide. As a result, it has been found that a polymer supposed to be substantially free from the irritation to organisms and to have an extremely high safety to organisms can be obtained by using an α-amino acid, which is one having a good adaptability and an extremely high safety to organisms, for the ring opening reaction of the polysuccinimide. In consequence, the present invention has been completed.

A technique whereby that the rings of the polysuccinimide are opened by using an α-amino acid, which is one having a good adaptability and an extremely high safety to organisms, has not been publicly known at all prior to the filing of the present application.

The reason why a technique whereby the rings of the polysuccinimide are opened by using an α-amino acid has not been publicly known at all prior to the filing of the present application, though it has been known that the α-amino acid has a good adaptability and an extremely high safety to organisms, is probably based on the fact that technical problems (e.g. the low solubility of α-amino acid in an organic solvent and the very low reactivity of the α-amino group) have not been solved yet.

Very few techniques whereby the rings of the polysuccinimide are opened by using an amino acid other than the α-amino acid have been publicly known before the filing of the present application. This reason is also probably based on technical problems regarding the solubility in an organic solvent and the low reactivity of an amino acid other than the α-amino acid.

With regard to the technique about using the amino acid, only Die Angewandte Makromolekulare Chemie-Applied Macromolecular Chemistry and Physics [Machado et al., Vol. 195, p. 35–56 (1992)] disclosed a technique whereby the rings of the polysuccinimide are opened by using Γ-aminobutyric acid (piperidic acid) which is Γ-amino acid or glycylglycine which is oligopeptide (dipeptide).

In the Machado et al technique, however, even if four equivalents of glycylglycine is charged to the reaction per one equivalent of the monomer unit of the polysuccinimide in the presence of a strongly basic catalyst, only 0.5 equivalent of glycylglycine actually takes part in the reaction. Consequently, the problem regarding low reactivity has not been solved yet.

SUMMARY OF THE INVENTION

An object of the present invention is to provide a novel polymer obtained by ring opening reaction of polysuccinimide with an amino acid derivative such as an α-amino acid derivative and which is characterized by having no irritation to organisms (e.g., eyes and skin). That is to say, the present inventors intend to provide a polymer which is not an irritant to organisms (e.g., eyes and skin) and which has an amino acid residue or an amino acid ester residue as a pendant group in at least a part of a monomer unit.

Furthermore, an object of the present invention is to provide a polymer which is useful in the manufacturing fields of medical supplies and health and beauty aids, for example, in applications such as carriers for drugs and perfumes.

In view of the above-mentioned problem of the prior art, the present inventors have intensively conducted investigations based on a conception to use a compound, which is safe to organisms and environments, for ring opening reaction of polysuccinimide. As a result, it has been found that a polymer which is substantially free from irritation to organisms and has an extremely high safety to organisms can be obtained by using an α-amino acid, which is one having a good adaptability and an extremely high safety to organisms (e.g., eyes and skin), for the ring opening reaction of the polysuccinimide. In consequence, the present invention has been completed.

Moreover, in view of the above-mentioned problem of the prior art, the present inventors have intensively conducted investigations for remarkably improving the reactivity of the amino acid in the ring opening reaction of the polysuccinimide. As a result, it has been found that the ring opening reaction of the polysuccinimide can be accomplished with an extremely high reactivity by using an α-amino acid ester in place of the α-amino acid having an extremely low reactivity used in the prior art. In consequence, the present invention has been completed.

Furthermore, the present inventors have intensively conducted investigations for obtaining a polymer having an amino acid residue or an amino acid ester residue as a pendant group in at least a part of a monomer unit. As a result, it has been found that an amino acid ester causes the rings of polysuccinimide to open and that an amino acid residue or the amino acid ester residue is introduced as a pendant group into at least a part of the monomer unit, by reacting an amino acid ester with the polysuccinimide under proper reaction conditions. In consequence, the present invention has been completed.

The reason why the use of the α-amino acid ester in place of the α-amino acid in the ring opening reaction of the polysuccinimide can remarkably improve the reactivity, is considered to be based on the fact that the α-amino acid ester obtained by an esterification of an amino acid has an extremely improved solubility in an organic solvent so that the reactivity of an α-amino group is also extremely improved.

The above-mentioned object of the present invention can be achieved by a polymer containing, in its molecule, at least one monomer unit selected from the group consisting of monomer units of chemically modified α type or β type polyaspartic acids or their salts represented by the following formula (I) or (II):

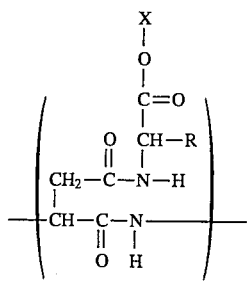
(I)

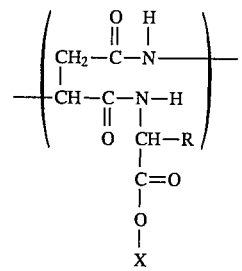
(II)

wherein R is an amino acid side chain, and X is independently an alkyl group, a cycloalkyl group, a benzyl group, a hydrogen atom or an alkali metal, as chemically modified polyaspartic acid monomer units.

In addition, the above-mentioned object of the present invention can be achieved by a process for preparing the polymer described above which comprises the step of reacting polysuccinimide comprising monomer units represented by the following formula (VI):

(VI)

wherein n is an integer of 10 or more, with at least one amino acid ester selected from the group consisting of amino acid esters represented by the following formula (VII):

(VII)

wherein R is an amino acid side chain, and X is an alkyl group, a cycloalkyl group or a benzyl group.

According to the present invention, there can be provided a novel polymer having an amino acid residue or an amino acid ester residue, which is not irritant to eyes and having excellent hair setting properties.

That is to say, the polymer having an amino acid residue or an amino acid ester residue as a pendant group in at least a part of a monomer unit according to the present invention, which can be obtained by reacting polysuccinimide with an amino acid ester in the presence or absence of a basic catalyst, is not an irritant to organisms (e.g., eyes and skin).

Therefore, the polymer regarding the present invention is characterized by having no irritation to the organisms (e.g., eyes and skin). For example, the polymer is useful in the industrial fields of medical supplies, health and beauty aids, and the like. Concretely, for example, the polymer is useful in the industrial fields of carriers for drugs, cosmetics, perfumes, surface active agents, food additives (thickeners, stabilizers, moisturizers, noodle modifiers, coagulants, pH adjustors, bacteriostats and the like). [The concepts of some terms which are used in the claims and the specification of the present application]

(1) The concept of the term "polymer":

In case that the polymer is a copolymer, the arrangement style of monomer units constituting the polymer may be any of random copolymer, alternating copolymer, block copolymer and graft copolymer. The polymer may be any of linear, large circular, branched, stellate and three-dimensional net-like.

(2) The concepts of the terms "cosmetics" and "perfumes":

The concepts of the terms "cosmetics" and "perfumes" which are used in the claims or the specification of the present application include, for example, kinds and articles described in "Table—Scope of kinds and effects of cosmetics" on pages 34 and 35 of "The 26th New Employee Cosmetics Technique Course Text" (Joint Sponsorship of Tokyo Cosmetics Industry Association and Tokyo Cosmetics Engineer Association, Cosponsorship of Foundation Japanese Cosmetics Association, Jun. 6, 1994, in Asahi Seimei Hall). All of the descriptions should be recognized as a part of the disclosure of the present specification because of clearly expressing the literature and the scope. They are the matters that a person skilled in the art can directly and inevitably recognize based on the disclosure in the present specification referring to the scope clearly expressed.

The concept of the term "cosmetics" used in the claims or the present specification include, for example, milky lotions, emulsions, creams, cleansing creams, face powders, lipsticks, face lotions, wet tissues, manicures, pedicures, moisturizers, facial packs, mousses, shaving creams, aftershaving lotions, hair tonics, hair liquids, hair sprays, deodorants, deodorizers, smell killers, and the like.

The concept of the term "perfumes" used in the claims or the specification of the present application include, for example, hair-dressings, scents, colognes, toilet waters, fragrances, bath agents, aromatics and the like.

DESCRIPTION OF THE PREFERRED EMBODIMENTS

Preparation process of polymer

The present invention is concerned with a polymer having an amino acid residue or an amino acid ester residue as a pendant group in at least a part of a monomer unit which can be obtained by reacting polysuccinimide with an amino acid ester in the presence or absence of a basic catalyst and which is free from irritation to organisms (e.g., eyes and skin).

A "process for preparing the polymer" regarding the present invention is characterized by dissolving the polysuccinimide in an organic solvent, and then adding an amino acid ester to the solution in the presence or absence of a basic catalyst to carry out the reaction.

Next, the "process for preparing the polymer" regarding the present invention will be described.

(1) Polysuccinimide:

No particular restriction is put on the preparation process of the polysuccinimide which is used in the "process for preparing the polymer" regarding the present invention.

The polysuccinimide which is used in the "process for preparing the polymer" regarding the present invention can usually be obtained by heating aspartic acid at 170 to 180° C. under reduced pressure in the presence of phosphoric acid to carry out dehydration condensation. If the polysuccinimide having a higher molecular weight is required, for example, the polysuccinimide obtained by the abovementioned procedure can be treated with a condensation agent such as dicyclohexylcarbodiimide.

(2) Organic solvent:

No particular restriction is put on the organic solvent which can be used in the "process for preparing the polymer" regarding the present invention, and any organic solvent can be used, so long as it can substantially dissolve the polysuccinimide and the amino acid ester and/or does not substantially impede the progress of the reaction.

Typical examples of the organic solvent include organic aprotic polar solvents such as dimethylformamide (DMF), dimethylacetamide (DMAc), N-methylpyrrolidone (NMP), dimethylimidazolidinone (DMI), dimethyl sulfoxide (DMSO) and sulfolane. They can be used singly or in combination.

(3) Kind of amino acid ester:

No particular restriction is put on the amino acid ester which is used in the "process for preparing the polymer" regarding the present invention, and any amino acid ester can be used, so long as it is substantially soluble in the organic solvent and/or does not substantially impede the progress of the reaction.

The formula of the amino acid ester can be represented by the following formula (VII'):

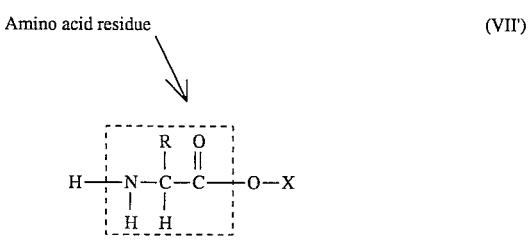

(4) Amino acid residue moiety of amino acid ester:

No particular restriction is put on the amino acid residue of the amino acid ester (VII').

Typical examples of the amino acid ester include esters having, in their molecules, as the amino acid residues, the residues of the amino acids which will be hereinafter exemplified. These esters can be used singly or in combination.

Typical examples of the amino acids include aliphatic amino acids such as glycine, alanine, valine, leucine and isoleucine; oxyamino acids such as serine and threonine; sulfur-containing amino acids such as methionine, cysteine and cystine; acidic amino acids such as aspartic acid and glutamic acid; basic amino acids such as lysine, ornithine and arginine; aromatic amino acids such as phenylalanine and tyrosine; heterocyclic amino acids such as tryptophan, histidine, proline and oxyproline; and amide group-containing amino acids such as asparagine and glutamine. These amino acids can be used irrespective of L-form, D-form and DL-form. In particular, the amino acid residue is preferably a glycine residue and/or a lysine residue.

(5) Ester moiety of amino acid ester:

No particular restriction is put on X in the formula (VII') of the amino acid ester, so long as X is any one of alkyl groups, cycloalkyl groups and a benzyl group.

Typical examples of the amino acid esters include aliphatic esters such as methyl esters, ethyl esters, butyl esters and hexyl esters; alicyclic esters such as cyclohexyl esters; and benzyl esters. They can be used singly or in combination. Of the amino acid esters, lower aliphatic esters such as methyl esters and ethyl esters are preferable, and methyl esters are more preferable.

The amino acid esters may be in the forms of free esters and mineral acid salts such as hydrochlorides and sulfates.

(6) Amount of amino acid ester to be used:

No particular restriction is put on the amount of the amino acid ester which is used in the "process for preparing the polymer" regarding the present invention, so long as it is substantially soluble in the organic solvent and/or does not substantially impede the progress of the reaction.

The amount of the amino acid ester is usually in the range of 0.1 to 10 equivalents, preferably 0.1 to 1.0 equivalent per one equivalent of the monomer unit of the polysuccinimide.

(7) Opening of imide rings by reaction with amino acid ester:

By the reaction of the polysuccinimide with the amino acid ester, the imide rings of the polysuccinimide can be opened.

When the ring opening reaction is carried out by using less than one equivalent of the amino acid ester per one equivalent of the monomer unit of the polysuccinimide, some unreacted imide rings usually remain.

If desired, the unreacted imide rings may remain as it is, or they may be opened by further ring opening reaction with the other amino acid ester. Furthermore, if desired, the unreacted imide rings may be opened by ring opening reaction with a substituted amine such as ethanolamine, cysteamine and dibutylamine.

(8) Opening of imide rings by alkali hydrolysis reaction:

By adding a base to polysuccinimide to effect an alkali hydrolysis reaction, the imide rings of the polysuccinimide can be opened.

Accordingly, the unopened imide rings of the polysuccinimide that remained in the ring opening reaction of the polysuccinimide with the amino acid ester, if desired, can be opened by subjecting them to the alkali hydrolysis reaction with an aqueous basic solution.

No particular restriction is put on the kind of alkali compound which is used in the alkali hydrolysis reaction, so long as it does not substantially lower the molecular weight of the polysuccinimide and can open the imide rings in the polysuccinimide molecules to a desired level.

Typical examples of the base, which is used to open the imide rings of the polysuccinimide by alkali hydrolysis reaction with an aqueous basic solution, include alkali metal hydroxides such as sodium hydroxide and potassium hydroxide; metal carbonates such as sodium carbonate and potassium carbonate; organic bases such as triethylamine, triethanolamine, N-methylmorpholine and diisopropylethylamine; and ammonia. They can be used singly or in combination. In general, a hydroxide such as sodium hydroxide can be used. The above-mentioned basic compounds are usually added as an aqueous basic solution.

(9) Process for preparing amino acid ester:

No particular restriction is put on the process for preparing the amino acid ester which is used in the "process for preparing the polymer" regarding the present invention.

In general, the amino acid ester which is used in the "process for preparing the polymer" regarding the present invention, can be prepared by heating amino acid in an excess alcohol in the presence of a mineral acid catalyst such as sulfuric acid or hydrochloric acid.

(10) Basic catalyst:

No particular restriction is put on a basic catalyst which can be optionally used in the "process for preparing the polymer" regarding the present invention, so long as it can substantially accelerate the reaction rate.

Typical examples of the basic catalyst include aliphatic tertiary amines such as trimethylamine, triethylamine, tripropylamine, tributylamine, diisopropylethylamine (DIEA), triethanolamine and triethylenediamine (DABCO); an alicyclic tertiary amines such as N-methylmorpholine; aromatic tertiary amines such as dimethylaniline and diethylaniline; and tetramethylguanidine. They can be used singly or in combination.

(11) Amount of basic catalyst to be used:

No particular restriction is put on the amount of the basic catalyst which can be used in the "process for preparing the polymer" regarding the present invention, so long as it can substantially accelerate the reaction rate.

The amount of the basic catalyst to be used is usually in the range of 0 to 2 equivalents per one equivalent of the amino acid ester.

When the amino acid ester is the mineral acid salt, a neutralization equivalent of a base is added.

(12) Reaction temperature:

No particular restriction is put on the reaction temperature which is employed in the "process for preparing the polymer" regarding the present invention, so long as it can substantially maintain the progress of the reaction.

In general, the reaction temperature is selected from a temperature range of 5 to 150° C. Room temperature is usually selected.

As the reaction temperature, the most suitable temperature for the amino acid ester used can be selected from the temperature range of 5° to 150° C.

(13) Concentration of reaction system:

No particular restriction is put on the concentration of the reaction system which is employed in the "process for preparing the polymer" regarding the present invention, so long as it can substantially maintain the progress of the reaction.

The concentration of the reaction system is selected in terms of the concentration of the polysuccinimide. In general, the concentration of the polysuccinimide is selected from a concentration range of 1 to 30% by weight.

As the concentration of the reaction system, the most suitable concentration for the amino acid ester used can be selected from a concentration range of 1 to 30% by weight.

(14) Structure of monomer unit:

No particular restriction is put on the ratio of an $\alpha$-amide type monomer unit to a $\beta$-amide type monomer unit which are contained in the polymer obtained by the "process for preparing the polymer" regarding the present invention.

In the polymer obtained by the "process for preparing the polymer" regarding the present invention, the $\alpha$-amide type monomer unit and the $\beta$-amide type monomer unit randomly exist in general.

ISOLATION PROCESS OF POLYMER

No particular restriction is put on the isolation process of the polymer from a reaction solution after the completion of the reaction which can be employed in the "process for preparing the polymer" regarding the present invention, so long as it permits the isolation of a reaction product in a desired purity.

The isolation may be carried out by any of known and already used methods. In general, a known and used isolation operation such as concentration, recrystallization or reprecipitation can be employed.

One typical example of the isolation methods is the following method. After the completion of the reaction, an excess in a poor solvent (e.g., methyl alcohol, ethyl alcohol, isopropyl alcohol or the like) is added to a reaction solution in which a reaction product is dissolved at a proper temperature. The deposited crystals of the reaction product are then isolated by decantation, filtration, suction filtration or the like. Afterward, the crystals are sufficiently washed with a poor solvent which does not dissolve the crystals, and then dried.

Another typical example of the isolation methods is the following method. After the completion of the reaction, a reaction solution in which a reaction product is dissolved is added to the same excess poor solvent as previously described at a proper temperature. The deposited crystals of the reaction product are then isolated, and the crystals are washed and then dried in the same manner as previously described.

[CONVERSION OF CARBOXYL GROUP OF PENDANT GROUP BY ALKALI HYDROLYSIS]

(1) Alkali hydrolysis reaction:

As described above, when a base is added to the polysuccinimide to carry out the reaction, the imide rings of the polysuccinimide can be opened.

Similar to the operation of this ring opening reaction, a basic compound is added to the polymer having an amino acid residue or an amino acid ester residue as a pendant group in at least a part of a monomer unit which can be obtained by the "process for preparing the polymer" regarding the present invention to carry out the alkali hydrolysis reaction, whereby a polymer can be obtained in which the carboxyl group of the pendant group is free or in the state of a salt.

The above-mentioned ring opening reaction and the reaction the of converting the carboxyl group of the pendant group can be simultaneously carried out by suitably setting the reaction conditions such as the kind of polymer having the amino acid residue or the amino acid ester residue as the pendant group in at least a part of the monomer unit, the kind and concentration of basic compound, the reaction temperature, the reaction time and the like.

(2) Kind of alkali compound:

No particular restriction is put on the kind of alkali compound which can be used in the above-mentioned alkali hydrolysis reaction, so long as it does not substantially lower the molecular weight of the polysuccinimide and can convert the carboxyl group of the pendant group to a desired level.

Typical examples of the base which can be used in the conversion of the carboxyl group of the pendant group by the alkali hydrolysis reaction include alkali metal hydroxides such as sodium hydroxide and potassium hydroxide; metal carbonates such as sodium carbonate and potassium carbonate; organic bases such as triethylamine, triethanolamine, N-methylmorpholine and diisopropylethylamine; and ammonia. They can be used singly or in combination.

In general, alkali metal hydroxides such as sodium hydroxide and potassium hydroxide are preferable. The above-mentioned basic compounds are usually added as an aqueous basic solution.

(3) Concentration of alkali compound:

As stated above, the above-mentioned alkali compound is usually added as an aqueous basic solution.

Regarding the above-mentioned alkali hydrolysis reaction, in case that the alkali compound is added as an aqueous basic solution, no particular restriction is put on the concentration of the alkali compound, so long as it does not substantially lower the molecular weight of the polysuccinimide and can convert the carboxyl group of the pendant group to a desired level.

In general, the concentration of the alkali compound is preferably in the range of 0.01 to 5N, more preferably 0.1 to 3N. If the concentration of the alkali compound is too low, the efficiency of the hydrolysis decreases. Conversely, if the concentration of the alkali compound is too high, hydrolysis of the main chaing and side chains, and a decrease of the molecular weight might occur inconveniently.

POLYMER

The present invention is concerned with a polymer having an amino acid residue or an amino acid ester residue as a pendant group in at least a part of a monomer unit which is free from irritation to organisms (e.g., eyes and skin).

No particular restriction is put on the preparation process of the "polymer" regarding the present invention.

The preferable embodiment of the preparation process of the "polymer" regarding the present invention is the aforesaid "preparation process of the polymer" regarding the present invention.

Next, the "polymer" regarding the present invention will be described.

(1) Structure of monomer unit:

No particular restriction is put on the ratio of an $\alpha$-amide type monomer unit (I') to a $\beta$-amide type monomer unit (II') which are contained in the molecule of "polymer" regarding the present invention.

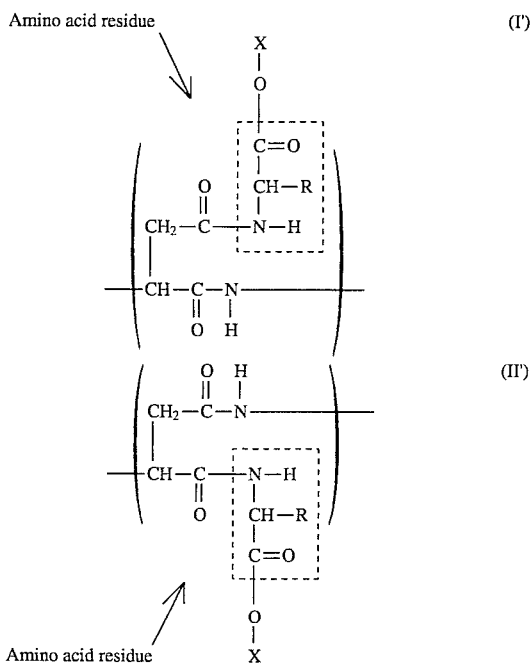

In the "polymer" regarding the present invention, the $\alpha$-amide type monomer unit and the $\beta$-amide type monomer unit randomly exist.

The weight-average molecular weight (Mw) of the polymer is usually in the range of 2,000 to 300,000, preferably 3,000 to 200,000, more preferably 5,000 to 100,000.

(2) Amino acid residue moiety as pendant group:

No particular restriction is put on the amino acid residue in the $\alpha$-amide type monomer unit (I') and the $\beta$-amide type monomer unit (II') contained in the "polymer" regarding the present invention.

Typical examples of the amino acid residue include the residues of the following amino acids. They can be used singly or in combination.

Typical examples of the amino acids include aliphatic amino acids such as glycine, alanine, valine, leucine and isoleucine; oxyamino acids such as serine and threonine; sulfur-containing amino acids such as methionine, cysteine and cystine; acidic amino acids such as aspartic acid and glutamic acid; basic amino acids such as lysine, ornithine and arginine; aromatic amino acids such as phenylalanine and tyrosine; heterocyclic amino acids such as tryptophan, histidine, proline and oxyproline; and amide group-containing amino acids such as asparagine and glutamine. These amino acids can be used irrespective of L-form, D-form and DL-form.

(3) Ester moiety of pendant group:

No particular restriction is put on an ester moiety X in the $\alpha$-amide type monomer unit (I') and the $\beta$-amide type monomer unit (II') contained in the "polymer" regarding the present invention, so long as X is any one of alkyl groups, cycloalkyl groups, a benzyl group, a hydrogen atom and alkali metals.

Typical examples of the ester moiety include aliphatic esters such as methyl esters, ethyl esters, butyl esters and hexyl esters; alicyclic esters such as cyclohexyl esters; and benzyl esters. They can be used singly or in combination.

As the ester moiety, lower aliphatic esters having 1 to 5 carbon atoms such as methyl esters and ethyl esters are preferable, and methyl esters are especially preferable.

Next, the present invention will be described in more detail with reference to experimental examples and a comparative example.

The description of synthetic examples, embodiments, examples and the like in this specification is intended to aid the grasp of the present invention, and it is not intended to limit the technical scope of the present invention.

PROCEDURES OF EVALUATION

The procedures of evaluation employed in the examples and the comparative example will be described in the following (1) to (6).

(1) Evaluation of weight-average molecular weight of polysuccinimide used as a raw material:

The weight-average molecular weight (hereinafter referred to as "Mw") of the polysuccinimide used as a raw material was evaluated in terms of polystyrene by gel permeation chromatography (hereinafter referred to as "GPC").

| | |
|---|---|
| Device: | Jasco Corp. 880-PU |
| Detector: | Shodex RID-300 |
| Column: | Shodex KD-804 + KD-80M |
| Solvent: | 0.01M LiBr/DMF |
| Conc.: | 0.5 wt % |
| Amount: | 20 μl |
| Flow rate: | 1.0 ml/min |

(2) Evaluation of weight-average molecular weight of polymer:

The Mw of the polymer was evaluated in terms of polyethylene oxide under the following conditions by GPC.

| | |
|---|---|
| Device: | Jasco Corp. 880-PU |
| Detector: | Jasco Corp. 830-RI |
| Column: | Shodex OHpak B-804 |
| Solvent: | Mixed solvent of 0.1M KCl/water:methanol = 8:2 |
| Conc.: | 0.5 wt % |
| Amount: | 20 μl |
| Flow rate: | 0.4 ml/min |

(3) Elemental analysis:

The elemental analysis was carried out in a usual manner.

(4) $^1$H nuclear magnetic resonance (NMR) analysis:

The NMR analysis was carried out in a usual manner.

(5) Curl retention test:

Straight hairs having a length of 32 cm were washed with a 0.25 wt % aqueous sodium lauryl sulfate solution, dried, and then bundled every 3 g.

The hairs were immersed in a 3 wt % aqueous polymer solution for one minute to uniformly apply the solution thereon, scraped with fingers five times to remove the excess polymer solution, wound onto a rod having a diameter of 1.4 cm, fixed with a rubber band, and then dried at 50° C. for 2 hours. The dried hairs were gently detached from the rod, and then hung in a constant temperature and constant humidity tank at 30° C. and at a relative humidity of 90%. Afterward, the length of the curl was measured with time, and a curl retention ratio (%) was then calculated in accordance with the following formula:

$$\text{Curl retention ratio }(\%) = (L-L_n)/(L-L_0) \times 100$$

wherein L is the length (cm) of the original straight hairs, $L_0$ is the length (cm) of the curl after 0 hour, and $L_n$ is the length (cm) of the curl after n hours.

(6) Rabbit eye mucosa irritation test (the Draize method):

A rabbit eye mucosa irritation test was carried out as follows.

(a) Preparation of sample: A sample was ground into fine powder in a mortar, and the used in the test.

(b) Number of used animals: Three male animals (unwashed eye group only) were used per analyte. Within 24 hours before the start of administration, it was confirmed by a fluorescein sodium solution treatment that the eyes of these animals were normal.

(c) Measurement of weight: The weight of each animal was measured immediately before the administration once on the administration day.

(d) Administration way: The lower eyelid of a right eye was gently separated from an eyeball, and 0.1 g of the sample was put in a conjuctival sac. Afterward, both the eyeballs were gently closed and then maintained for about one second. The left eye was not treated, and so it was regarded as a control.

(e) Mark: After 24, 48 and 72 hours and after 5, 7, 14 and 21 days from the administration of the sample, the irritation states of the eyes were observed in accordance with the following table (the OECD method) to decide the mark of the irritation states. Cornea, iris and conjunctivae were observed, and other damages were also observed.

Furthermore, on the basis of the obtained results, the strength of the irritation was judged in accordance with the classification of eye irritation evaluation (Federal register, 1972).

| Rabbit eye mucosa irritation test mark table (the OECD method) | | | |
|---|---|---|---|
| Part to be evaluated | Mark | Positive | State of eye by irritation |
| 1 Cornea (The opacity mark of the cornea is evaluated in a portion in which the opacity is densest.) | 0 | Negative | No ulceration or opacity. |
| | 1 | Positive | Cornea: Scattered or diffuse areas of opacity (which is different from a usual light opacity state). Details of iris: Clearly visible. |
| | 2 | Positive | Cornea: Easily discernible translucent areas of opacity. Details of iris: Slightly obscured. |
| | 3 | Positive | Cornea: Nacreous areas of opacity. Details of iris: They are not visible, and size of pupil is barely discernible. |
| | 4 | Positive | The iris is not discernible. |
| 2 Iris | 0 | Negative | Normal |

-continued

Rabbit eye mucosa irritation test mark table (the OECD method)

| Part to be evaluated | Mark | Positive | State of eye by irritation |
|---|---|---|---|
| | 1 | Positive | Any of markedly deepened folds, congestion, swilling, moderate circumcorneal injection is discernible. The iris reacts to light. |
| | 2 | Positive | Any of no reaction to light, hemorrhage and marked tissue destruction is discernible. |
| 3 Conjunctivae (which is evaluated by the redness of palpebral and bulbar conjunctivae excluding the cornea and the iris) | 0 | Negative | Vessels are normal |
| | 1 | Positive | Some vessels are definitely injected. |
| | 2 | Positive | Diffuse crimson red is shown, and individual vessels are not easily discernible. |
| | 3 | Positive | Diffuse beefy red is shown. |
| 4 Chemasis | 0 | Negative | No swelling |
| | 1 | Positive | Slight swelling (which includes nictitating membrane) |
| | 2 | Positive | Obvious swelling with partial eversion of lids. |
| | 3 | Positive | Swelling with lids about half closed. |
| | 4 | Positive | Swelling with lids more than half closed. |

EXAMPLE 1

(1) Reaction:

As a reactor, there was used a separable flask equipped with a stirrer, a heater, a thermometer and a nitrogen line. From reaction to isolation, the temperature of a system was maintained at 20° to 25° C. During the reaction, the reaction system was sufficiently stirred.

As a raw material, polysuccinimide having a weight-average molecular weight of 62,000 was used.

29.1 g (0.3 mol) of the polysuccinimide was dissolved in 174.7 g of DMF, and the mixture was then poured into the reactor together with 37.7 g (0.3 mol) of glycine methyl ester hydrochloride.

Afterward, 60.7 g (0.6 mol) of triethylamine was continuously added dropwise to the reactor over 2 hours to carry out reaction, and after the addition, the reaction was further continued for 29 hours.

After the completion of the reaction, the resultant reaction solution was filtered with suction to remove a by-product, i.e., triethylamine hydrochloride, as a filter residue (hereinafter referred to as "filter mass"), and the filtrate containing a produced polymer was fed to a next isolation step.

(2) Isolation:

The filtrate was poured with stirring into 2,500 ml of ethanol which was a poor solvent for the produced polymer, thereby precipitating the produced polymer.

The suspension of the produced polymer was filtered with suction to isolate the produced polymer in the form of a mass.

Furthermore, this mass was dispersed in the poor solvent, stirred and then filtered with suction, and this serial operation was then repeated several times to sufficiently wash the produced polymer.

Afterward, the produced polymer was dried by hot air at 60° C. to obtain the produced polymer isolated.

The produced polymer thus isolated was subjected to evaluation described hereinafter, the curl retention test and the rabbit eye mucosa irritation test.

(3) Weight-average molecular weight and yield:

The weight-average molecular weight of the produced polymer was 19,000.

The yield of the produced polymer was 48.4 g (yield: 86.8%).

(4) Elemental analysis:

The unit molecular formula and the elemental analysis values of the produced polymer were as follows:

| Unit molecular formula: $C_7H_{10}N_2O_4$ Elemental analysis values: | | |
|---|---|---|
| | Calc. | Found |
| C | 45.16 | 45.97 |
| H | 5.40 | 5.49 |
| N | 15.05 | 14.48 |

(5) $^1$H-NMR analysis (monomer unit of produced polymer):

For the produced polymer, $^1$H-NMR was measured, and as a result, the following peaks were detected.

8.4 ppm (—CONH—)

4.5 ppm ($CH_2$)

3.8 ppm (CH)

Neither of a peak at 5.1 ppm inherent in a methylene group ([CH2-PSI]) of a succinimide monomer unit and a peak at 3.2 ppm inherent in a methine group ([CH-PSI]) of the another succinimide monomer unit were detected. Consequently, it can be considered that a polysuccinimide monomer unit is not substantially present in the molecule of the produced polymer.

Here, PSI means the polysuccinimide.

Therefore, the monomer unit of the polymer obtained in Example 1 can be considered to be substantially constituted only of the following α-amide type monomer unit (Ia) and β-amide type monomer unit (IIa).

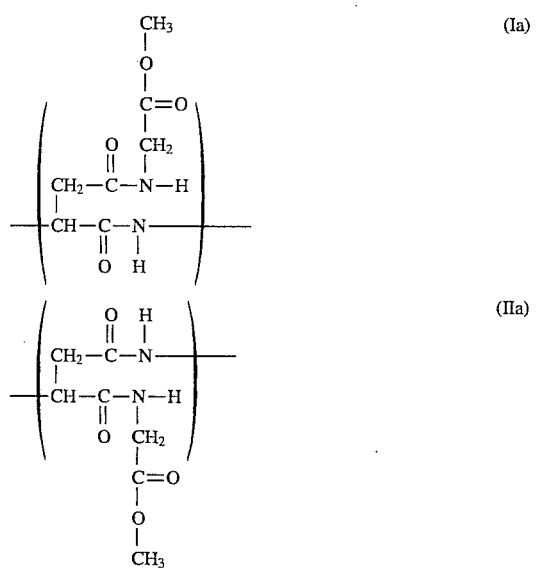

COMPARATIVE EXAMPLE 1

(1) Reaction:

The same reactor as in Example 1 was used. From reaction to isolation, the temperature of a system was maintained at 20 to 25° C., and the reaction system was sufficiently stirred during the reaction as in Example 1. Oxygen was removed from the reaction system by dry nitrogen bubbling which operation is different from Example 1.

As a raw material, polysuccinimide having a weight-average molecular weight of 62,000 was used.

Beforehand, a cysteamine/DMF suspension and a polysuccinimide/DMF solution were prepared. That is to say, there were beforehand prepared the cysteamine/DMF suspension in which 8.2 g (0.106 mol) of cysteamine was suspended in 32.0 g of DMF, and the polysuccinimide/DMF solution in which 10.0 g (0.103 mol) of the polysuccinimide was dissolved in 40.0 g of DMF. Oxygen in the DMF used herein had been sufficiently removed by dry nitrogen bubbling.

The above-mentioned cysteamine/DMF suspension was poured into the reactor. The above-mentioned polysuccinimide/DMF solution was continuously added dropwise to the reactor over 0.5 hour to carry out reaction, and after the addition, the reaction was further continued for 24 hours.

(2) Isolation:

The reaction solution was poured with stirring into 400 ml of methanol which was a poor solvent for a produced polymer, thereby precipitating the produced polymer.

The suspension of the produced polymer was filtered with suction to isolate the produced polymer in the form of a mass.

Furthermore, this mass was dispersed in the poor solvent, stirred and then filtered with suction, and this serial operation was then repeated several times to sufficiently wash the produced polymer. Afterward, the produced polymer was dried by hot air at 60° C. to isolate the produced polymer.

The produced polymer thus isolated was subjected to evaluation described hereinafter, the curl retention test and the rabbit eye mucosa irritation test.

(3) Weight-average molecular weight and yield:

The yield of the produced polymer was 14.7 g (yield: 82.3%).

(4) Elemental analysis:

The unit molecular formula and the elemental analysis values of the produced polymer were as follows:

| Unit molecular formula: $C_6H_{10}N_2O_2S$ Elemental analysis values: | | |
|---|---|---|
| | Calc. | Found |
| C | 41.37 | 41.22 |
| H | 5.74 | 5.65 |
| N | 16.09 | 16.00 |

(5) Monomer unit of the produced polymer: The monomer unit of the polymer obtained in Comparative Example 1 can be considered to be substantially constituted only of the following α-amide type monomer unit (VIII) and β-amide type monomer unit (IX).

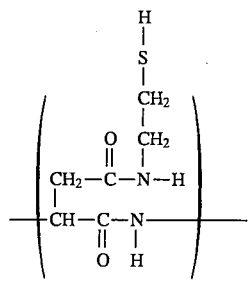

(VIII)

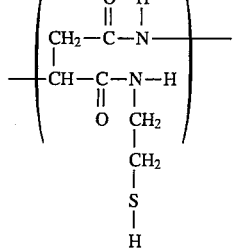

(IX)

Curl retention test

For the polymers obtained in Example 1 and Comparative Example 1, a curl retention test was carried out. The results are shown in Table 1.

TABLE 1

| | Curl retention ratio (%) | | | | | |
|---|---|---|---|---|---|---|
| | Time (hr) | | | | | |
| | 0.5 | 1.0 | 2.0 | 3.0 | 4.0 | 5.0 |
| Example 1 | 60 | 52 | 48 | 42 | 38 | 30 |
| Comp. Ex. 1 | 24 | 18 | 10 | 5 | 2 | 2 |
| Blank | 5 | 0 | 0 | 0 | 0 | 0 |

Rabbit eye mucosa irritation test

For the polymers obtained in Example 1 and Comparative Example 1, a rabbit eye mucosa irritation test was carried out. The results are shown in Table 2.

TABLE 2

| Rabbit eye mucosa irritation test. | | | | | | | |
|---|---|---|---|---|---|---|---|
| | Hours after administration | | | | | | |
| | 24 hrs | 48 hrs | 72 hrs | 5 days | 7 days | 14 days | 21 days |
| Ex. 1 Cornea opacity | 0 | 0 | 0 | 0 | 0 | 0 | 0 |
| Iris abonormal | 0 | 0 | 0 | 0 | 0 | 0 | 0 |
| Conjuctivae redness | 0.3 | 0 | 0 | 0 | 0 | 0 | 0 |
| Chemasis | 0 | 0 | 0 | 0 | 0 | 0 | 0 |
| Cx. 1 Cornea opacity | 1.3 | 1.3 | 1.3 | 0.7 | 0.7 | 1.0 | 1.3 |
| Iris abonormal | 0 | 0.7 | 0.7 | 0 | 0 | 0 | 0 |
| Conjuctivae redness | 2.0 | 2.3 | 1.7 | 1.3 | 1.3 | 1.3 | 0 |
| Chemasis | 3.7 | 1.7 | 1.7 | 1.3 | 1.3 | 1.3 | 1.3 |

As is apparent from comparison between Example 1 and Comparative Example 1 shown in Table 1, the polymer regarding the present invention has excellent hair setting properties.

As is apparent from comparison between Example 1 and Comparative Example 1 shown in Table 2, the polymer regarding the present invention has no irritation to the eye mucosa.

EXAMPLE 2

(1) Reaction:

The same procedure as in Example 1 was carried out except that 29.1 g (0.3 mol) of polysuccinimide, 18.8 g (0.15 mol) of glycine hydrochloride methyl ester and 30.4 g (0.3 mol) of triethylamine were used, to carry out reaction, thereby obtaining a polymer.

(2) Isolation:

The same procedure as in Example 1 was carried out except that 2,750 ml of ethanol was used, to isolate the polymer.

(3) Weight-average molecular weight and yield:

The weight-average molecular weight of the produced polymer was 23,000.

The yield of the produced polymer was 39.5 g (yield: 93.0%).

(4) Elemental analysis:

The unit molecular formula and the elemental analysis values of the produced polymer were as follows:

| Unit molecular formula: $(C_7H_{10}N_2O_4)_{0.5}$-$(C_4H_3NO_2)_{0.5}$ Elemental analysis values: | | |
|---|---|---|
| | Calc. | Found |
| C | 47.30 | 47.13 |
| H | 4.25 | 4.51 |
| N | 14.74 | 14.66 |

(5) $^1$H-NMR analysis (monomer unit of produced polymer):

For the produced polymer, $^1$H-NMR was measured, and as a result, the following peaks were detected.

8.4 ppm (—CONH—)

5.1 ppm (CH$_2$—PSI)

4.5 ppm (CH$_2$)

3.8 ppm (CH)

3.2 ppm (CH—PSI)

A peak at 5.1 ppm inherent in [CH2-PSI] and a peak at 3.2 ppm inherent in [CH-PSI] were detected. Consequently, it can be considered that a polysuccinimide monomer unit is also substantially present in the molecule of the produced polymer.

EXAMPLE 3

(1) Reaction:

The same operations as in "(1) Reaction" and "(2) Isolation" of Example 1 were conducted to obtain a polymer.

(2) Alkali treatment:

9.3 g (0.05 mol) of the polymer obtained in the above-mentioned step (1) was dissolved in 55.8 g of pure water, and 12.92 g (0.052 mol) of a 4N aqueous NaOH solution was then continuously added dropwise at 45° to 50° C. over 2 hours to carry out an alkali treatment.

This alkali treated solution was concentrated to 22 g, and then fed to the following isolation operation.

(3) Isolation:

The reaction solution was poured with stirring into 400 ml of methanol which was a poor solvent for the alkali treated polymer, thereby precipitating the alkali treated polymer.

The suspension of the alkali treated polymer was filtered with suction to isolate the alkali treated polymer in the form of a mass.

Furthermore, this mass was dispersed in the poor solvent, stirred and then filtered with suction, and this serial operation was then repeated several times to sufficiently wash the alkali treated polymer.

Afterward, the alkali treated polymer was dried by hot air at 60° C. to isolate the produced polymer.

The produced polymer thus isolated was evaluated.

(4) Weight-average molecular weight and yield:

The weight-average molecular weight of the alkali treated polymer was 56,000.

The yield of the alkali treated polymer was 2.78 g.

(5) Elemental analysis:

The unit molecular formula and the elemental analysis values of the produced polymer were as follows:

| Unit molecular formula: $C_6H_7N_2O_4Na$ Elemental analysis values: | | |
|---|---|---|
| | Calc. | Found |
| C | 37.12 | 37.24 |
| H | 3.63 | 4.01 |
| N | 14.43 | 14.14 |

The monomer unit of the polymer obtained in Example 3 can be considered to be substantially constituted only of the following units (Ib) and (IIb).

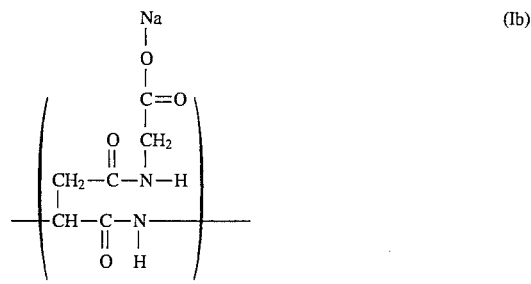

(Ib)

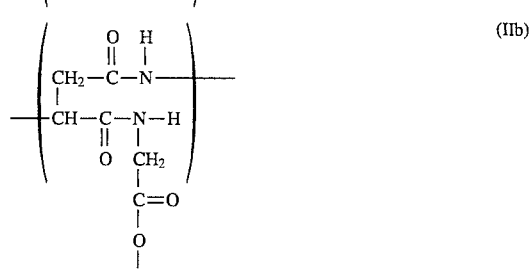

(IIb)

EXAMPLE 4

(1) Reaction:

The same reactor as in Example 1 was used. From reaction to isolation, the temperature of a system was maintained at 20° to 25° C., and the reaction system was sufficiently stirred during the reaction as in Example 1.

As a raw material, polysuccinimide having a weight-average molecular weight of 62,000 was used.

29.1 g (0.3 mol) of the polysuccinimide was dissolved in 174.7 g of DMF, and the mixture was then poured into the reactor together with 69.9 g (0.3 mol) of lysine methyl ester dihydrochloride.

Afterward, 91.1 g (0.9 mol) of triethylamine was continuously added dropwise to the reactor over 2 hours to carry out reaction, and after the addition, the reaction was further continued for 7 hours.

Comparative Example 1

After the completion of the reaction, the resultant reaction solution was filtered with suction to remove a by-product, i.e., triethylamine hydrochloride, as a filter residue (hereinafter referred to as "filter mass"), and the filtrate containing a produced polymer was fed to a next isolation step.

(2) Isolation:

The same operation as in "(2) Isolation" of Example 1 was carried out to isolate the polymer.

(3) Weight-average molecular weight and yield:

The weight-average molecular weight of the produced polymer was 48,000. The yield of the produced polymer was 29.7 g.

(4) Elemental analysis:

The unit molecular formula and the elemental analysis values of the produced polymer were as follows:

| Unit molecular formula: $C_{11}H_{19}N_3O_4$ Elemental analysis values: | | |
| --- | --- | --- |
| | Calc. | Found |
| C | 51.36 | 50.79 |
| H | 7.39 | 7.36 |
| N | 16.34 | 15.92 |

The monomer unit of the polymer obtained in Example 4 can be considered to be substantially constituted only of the same α-amide type monomer unit and β-amide type monomer unit as in Example 1 except that it has the residue of the lysine methyl ester dihydrochloride.

What is claimed is:

1. A polymer containing, in its molecule, at least one monomer unit selected from the group consisting of monomer units of chemically modified α type or β type polyaspartic acids or their salts represented by the following formula (I) or (II):

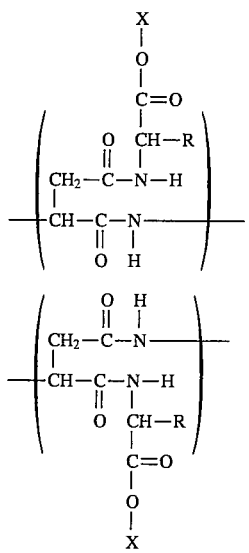

wherein R is an amino acid side chain, and X is independently an alkyl group having 1 to 6 carbon atoms, a cycloalkyl group, a benzyl group, a hydrogen atom or an alkali metal, as chemically modified polyaspartic acid monomer units.

2. The polymer according to claim 1 which further contains, in its molecule, at least one monomer unit selected from the group consisting of polysuccinimide monomer unit represented by the following formula (III):

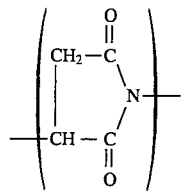

and monomer units of α type or β type polyaspartic acids or their salts represented by the following formula (IV) or (V):

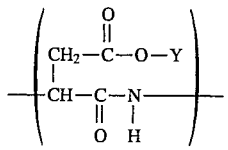

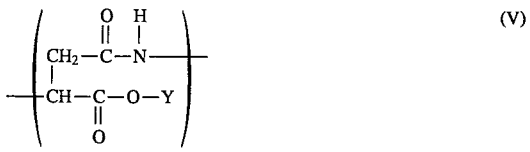

wherein Y is independently a hydrogen atom or an alkali metal, as monomer units which are not chemically modified.

3. The polymer according to claim 1 wherein X in the formula (I) and/or (II) representing the monomer units of the chemically modified polyaspartic acids or their salts is an alkyl group having 1 to 5 carbon atoms.

4. The polymer according to claim 3 wherein X in the formula (I) and/or (II) representing the monomer units of the chemically modified polyaspartic acids or their salts is at least one selected from the group consisting of methyl group, ethyl group, propyl group, isopropyl group, butyl group and isobutyl group.

5. A process for preparing the polymer described in claim 1 which comprises the step of reacting polysuccinimide comprising monomer units represented by the following formula (IV):

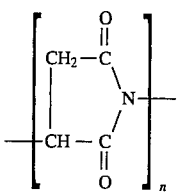

wherein n is an integer of 10 or more, with at least one amino acid ester selected from the group consisting of amino acid esters represented by the following formula (VII):

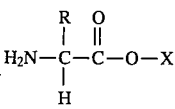

wherein R is an amino acid side chain, and X is an alkyl group having 1 to 6 carbon atoms, a cycloalkyl group or a benzyl group.

6. The process for preparing the polymer according to claim 5, wherein the polysuccinimide is reacted with the amino acid ester in the presence of a basic catalyst which accelerates the rate of reaction between the polysuccinimide and the amino acid ester.

7. The process for preparing the polymer according to claim 5 wherein the amino acid residue of the amino acid ester is a glycine residue or a lysine residue.

* * * * *

UNITED STATES PATENT AND TRADEMARK OFFICE
CERTIFICATE OF CORRECTION

PATENT NO. : 5,571,889
DATED : November 5, 1996
INVENTOR(S) : Toshio KATOH et al It is certified that error appears in the above-identified patent and that said Letters Patent is hereby corrected as shown below:

On the title page, item [56], add the following:
4,363,797   12/82   Jacquet et al.   ..............424/70

Signed and Sealed this

Twenty-fifth Day of November, 1997

Attest:

BRUCE LEHMAN

*Attesting Officer*         *Commissioner of Patents and Trademarks*